US012800391B2

(12) United States Patent
Yin et al.

(10) Patent No.: US 12,800,391 B2
(45) Date of Patent: Nov. 17, 2026

(54) GENERATION OF MULTISPECTRAL IMAGING INFORMATION USING ANALYTICAL MULTISPECTRAL IMAGING

(71) Applicant: Alcon Inc., Fribourg (CH)

(72) Inventors: Lu Yin, Keller, TX (US); Ramesh Sarangapani, Coppell, TX (US); Kongfeng Berger, San Jose, CA (US); Vignesh Suresh, Arlington, TX (US)

(73) Assignee: Alcon Inc., Fribourg (CH)

( * ) Notice: Subject to any disclaimer, the term of this patent is extended or adjusted under 35 U.S.C. 154(b) by 455 days.

(21) Appl. No.: 18/463,088

(22) Filed: Sep. 7, 2023

(65) Prior Publication Data

US 2024/0094054 A1 Mar. 21, 2024

Related U.S. Application Data

(60) Provisional application No. 63/406,615, filed on Sep. 14, 2022.

(51) Int. Cl.
*G01J 3/28* (2006.01)
*A61B 3/14* (2006.01)
(Continued)

(52) U.S. Cl.
CPC .............. *G01J 3/2823* (2013.01); *A61B 3/14* (2013.01); *G01J 3/10* (2013.01); *G01J 3/433* (2013.01);
(Continued)

(58) Field of Classification Search
CPC .... G01J 3/2823; G01J 2003/2826; G01J 3/10; G01J 3/433; G01J 2003/102; G01J 2003/4334; A61B 3/14; A61B 3/10
See application file for complete search history.

(56) References Cited

U.S. PATENT DOCUMENTS 7,246,905 B2 7/2007 Benedikt
9,185,357 B2 11/2015 Boccara
(Continued)

FOREIGN PATENT DOCUMENTS

CN 112816420 A 5/2021
WO 9916353 A1 4/1999
(Continued)

OTHER PUBLICATIONS

The RGB Digital Camera's Multi-Channel Spectral Reconstruction Based on Basis Function Theory, Zhu Yuanhong (Year: 2011).*
(Continued)

*Primary Examiner* — Tarifur R Chowdhury
*Assistant Examiner* — Carlos Perez-Guzman

(57) ABSTRACT

In certain embodiments, a system, a computer-implemented method, and computer-readable medium for generating multispectral imaging (MSI) based on performing an analytical MSI operation are described. The analytical MSI operation includes synchronizing a scan of a target by a broadband imaging device with a generation of a plurality of light signals, from a plurality of broadband illumination sources, directed towards the target. A set of spectral information associated with the target is generated, based on the scan of the target with the broadband imaging device. A set of multispectral imaging (MSI) information associated with the target is generated, based on performing an MSI operation using at least the set of spectral information. Ophthalmic information is determined based on the set of MSI information.

18 Claims, 13 Drawing Sheets

(51) Int. Cl.
*G01J 3/10* (2006.01)
*G01J 3/433* (2006.01)

(52) U.S. Cl.
CPC . *G01J 2003/102* (2013.01); *G01J 2003/2826* (2013.01); *G01J 2003/4334* (2013.01)

(56) References Cited

U.S. PATENT DOCUMENTS

| | | | |
|---|---|---|---|
| 2004/0085542 | A1 | 5/2004 | Soliz et al. |
| 2006/0140497 | A1 | 6/2006 | Kondo et al. |
| 2007/0156021 | A1 | 7/2007 | Morse et al. |
| 2010/0085537 | A1 | 4/2010 | Ramella-roman et al. |
| 2012/0065518 | A1 | 3/2012 | Mangoubi |
| 2013/0128227 | A1 | 5/2013 | Cui et al. |
| 2014/0002793 | A1 | 1/2014 | Hogan |
| 2014/0276025 | A1 | 9/2014 | Durbin |
| 2014/0300864 | A1 | 10/2014 | Fukuma |
| 2015/0015692 | A1 | 1/2015 | Smart |
| 2016/0278678 | A1 | 9/2016 | Valdes et al. |
| 2016/0338588 | A1 | 11/2016 | Friedman |
| 2016/0360958 | A1 | 12/2016 | Tsuri |
| 2017/0042464 | A1 | 2/2017 | Verdooner |
| 2017/0059408 | A1 | 3/2017 | Korner et al. |
| 2017/0176336 | A1* | 6/2017 | Dimitriadis .......... A61B 5/0071 |
| 2017/0297144 | A1 | 10/2017 | Nakanishi |
| 2018/0136486 | A1 | 5/2018 | Macnamara |
| 2019/0298170 | A1 | 10/2019 | Artal Soriano et al. |
| 2019/0343384 | A1 | 11/2019 | Plaian |
| 2021/0169324 | A1 | 6/2021 | Tripathi et al. |
| 2022/0151568 | A1 | 5/2022 | Yao |
| 2022/0157470 | A1 | 5/2022 | Sylvestre |
| 2022/0160228 | A1* | 5/2022 | Leahy ................ A61B 5/14555 |
| 2022/0225877 | A1 | 7/2022 | Shiba et al. |
| 2022/0240779 | A1 | 8/2022 | Peyman |
| 2022/0260413 | A1 | 8/2022 | Perruchot et al. |
| 2023/0018494 | A1 | 1/2023 | Gribble et al. |
| 2023/0113897 | A1* | 4/2023 | Deliwala .............. A61B 5/0075 356/317 |
| 2024/0415383 | A1 | 12/2024 | Shaked et al. |
| 2025/0150564 | A1 | 5/2025 | Mizutani et al. |

FOREIGN PATENT DOCUMENTS

| | | | |
|---|---|---|---|
| WO | 2015023990 | A1 | 2/2015 |
| WO | 2020047594 | A1 | 3/2020 |
| WO | 2021151046 | A1 | 7/2021 |
| WO | 2022011420 | A1 | 1/2022 |
| WO | 2022153320 | A1 | 7/2022 |

OTHER PUBLICATIONS

William R. Johnson, Snapshot hyperspectral imaging in ophthalmology, Journal of Biomedical Optics, 12 (1), 014036_1-7, 2007.

Ayon Dey, Machine learning algorithms: a review, International jurnal of computer science and information technologies, vol. 7, pp. 1174-1179, 2016.

Chen Qingyu et al., Multi-modal, multi-task, multi-attention (M3) deep learning detection of regular pseudodrusen: towards automated accessible classification of age-related macular degeneration, pp. 1-31, 2020URL:https://arxiv.org/abs/2011.05142vl.

Citation: M. Arsalan et al., Segmenting Retinal Vessels Using a Shallow Segmentation Network to Aid Ophthalmic Analysis, Mathematics, vol. 10, p. 1536, 2022.

J. Fhima et al., PVBM: A Python Vasculature Biomarker Toolbox Based on Retinal Blood Vessel Segmentation, Cornell University, 2022.

Sarraf David et al.,Retinal pigment epithelial tears in the era of intravitreal pharmacotherapy: risk factors, pathogenesis, prognosis and treatment (an American Ophthalmological Society thesis), American Ophthalmological Society, Transactions, vol. 112, pp. 142-159, 2014.

Yonlong He, et al., Segmenting Diabetic Retinopathy Lesions in Multispecial Images Using Low-Dimensional Spatial-Spectral Matrix Representation, Ieee Juournal of Biomedical and helth informatics, Ieee, Piscataway, NJ, USA, vol. 24, No. 2, pp. 493-502, Apr. 20, 2019.

Yoon Jonghee, @Hyperspectrial Imaging for Clinical Applications@ Biochip Journal, Korean Biochip, Seoul, South Korea, vol. 16, No. 1, Jan. 4, 2022, pp. 1-12.

* cited by examiner

GENERATION OF MULTISPECTRAL IMAGING INFORMATION USING ANALYTICAL MULTISPECTRAL IMAGING

BACKGROUND

Many microsurgical procedures require precision cutting and/or removal of various body tissues. For example, vitreoretinal procedures such as retinotomies, retinectomies, autologous retinal transplants, and vitrectomies typically require the cutting, removal, dissection, delamination, coagulation, or other manipulation of intraocular tissues such as the retina, vitreous humor, traction bands, and membranes.

Many of these intraocular tissues serve crucial roles in enabling vision. For example, the retina, or the innermost layer lining the back wall of the eye, is responsible for receiving, modulating, and transmitting visual stimuli from the external environment to the optic nerve, and ultimately, the visual cortex of the brain. Structurally, the retina is a complex and delicate tissue with numerous types of cells arranged in multiple cellular layers. Due to the retina's role in vision and its fragility, damage thereto may result in severe loss of vision or even permanent blindness. Therefore, cutting, removal, or other manipulation of the retina should be done with great care to avoid unwanted retinal trauma.

Some imaging systems may employ multispectral imaging (MSI) to provide surgeons (and/or other clinicians) with information related to spectral parameters of eye tissues/structures. MSI is a technique that involves measuring (or capturing) light from samples (e.g., eye tissues/structures) at different wavelengths or spectral bands across the electromagnetic spectrum. MSI may capture more information from the samples that may not be visible through conventional imaging, which generally uses broadband illumination and a broadband imaging sensor. In an exemplary MSI imaging system, the MSI information obtained by the MSI imaging system may be used to enable real-time adjustment in the use of instruments (e.g., forceps, lasers, probes, etc.) used to manipulate eye tissues/structures during surgery.

Currently, however, imaging systems typically have to use highly specialized and costly equipment in order to implement MSI. For example, to implement MSI, the illumination generally has to be tunable and/or the camera has be able to sense multiple spectral bands. Consequently, conventional imaging systems generally employ highly specialized multi-spectral illumination sources and/or highly specialized multi-spectral cameras in order to implement MSI. However, given the high costs associated with surgical procedures, such highly specialized and costly equipment may make implementing MSI for surgical procedures impractical.

Accordingly, it is beneficial to provide improved systems, devices, and methods for generating MSI to obtain ophthalmic information associated with various eye tissues/structures.

SUMMARY

In certain embodiments, a system is provided. The system includes an illumination device, a broadband imaging device, a memory comprising executable instructions, and a processor in data communication with the memory. The illumination device includes a plurality of broadband illumination sources, and the broadband imaging device includes a plurality of imaging sensors. The processor is configured to execute the executable instructions to synchronize a scanning of a target by the broadband imaging device with a generation of a plurality of light signals, from the plurality of broadband illumination sources, directed towards the target. The processor is also configured to execute the executable instructions to generate a set of spectral information associated with the target, based on the scanning of the target with the broadband imaging device. The processor is also configured to execute the executable instructions to generate a set of multispectral imaging (MSI) information associated with the target, based on performing an MSI operation using at least the set of spectral information. The processor is further configured to execute the executable instructions to determine ophthalmic information based on the set of MSI information.

In certain embodiments, a computer-implemented method is provided. The computer-implemented method includes synchronizing a scan of a target by a broadband imaging device with a generation of a plurality of light signals, from a plurality of broadband illumination sources, directed towards the target. The computer-implemented method also includes generating a set of spectral information associated with the target, based on the scan of the target with the broadband imaging device. The computer-implemented method also includes generating a set of multispectral imaging (MSI) information associated with the target, based on performing an MSI operation using at least the set of spectral information. The computer-implemented method further includes determining ophthalmic information based on the set of MSI information.

In certain embodiments, a non-transitory computer-readable medium is provided. The non-transitory computer-readable medium has computer executable instructions stored thereon. The computer executable instructions are executable by one or more processors to perform an operation. The operation includes synchronizing a scan of a target by a broadband imaging device with a generation of a plurality of light signals, from a plurality of broadband illumination sources, directed towards the target. The operation also includes generating a set of spectral information associated with the target, based on the scan of the target with the broadband imaging device. The operation further includes generating a set of multispectral imaging (MSI) information associated with the target, based on performing an MSI operation using at least the set of spectral information. The operation further includes determining ophthalmic information based on the set of MSI information.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
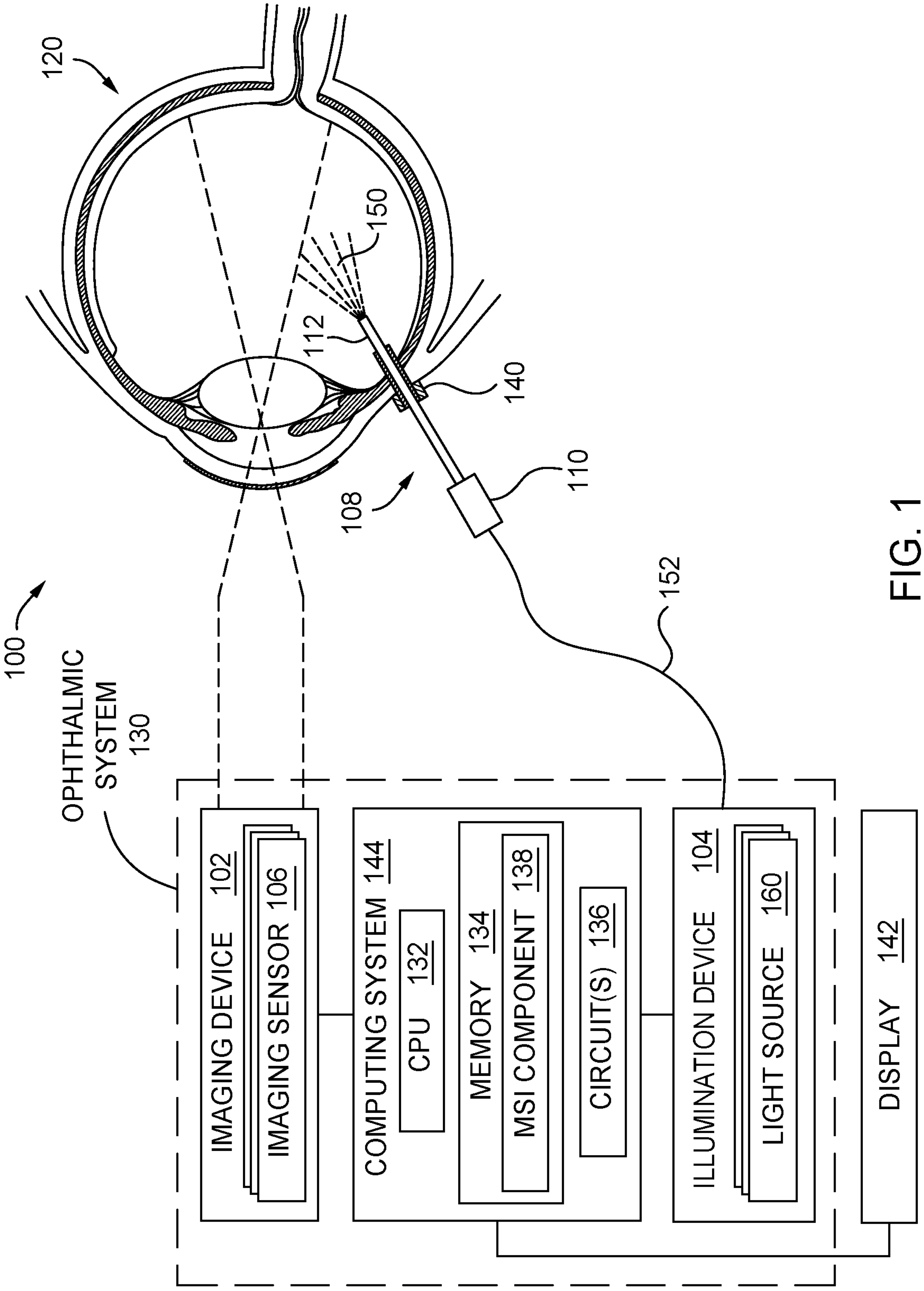
FIG. 1 illustrates an example system for generating MSI information based on an analytical MSI operation, according to certain embodiments.

Embodiments described herein provide ophthalmic systems, devices, and techniques for generating MSI information associated with a patient's eye based on performing an analytical MSI operation. In certain embodiments, the analytical MSI operation is performed with the use of non-MSI specialized equipment, such as broadband illumination source(s), a broadband imaging sensor(s) (also referred to as a broadband camera(s)), etc., as opposed to MSI specialized equipment, such as a multi-spectral band illumination source, a multi-spectral band camera, etc.

In certain embodiments described below, the analytical MSI operation involves assigning reflectance spectra of imaged features into multiple spectral bands based on one or more parameters of the non-MSI specialized equipment. Because non-MSI specialized equipment may not be configured (or designed) to implement MSI (e.g., the broadband illumination devices may not be tunable, the broadband imaging device may not be able to sense multiple (e.g., 3 or more) spectral bands, etc.), certain embodiments use parameter(s) of the non-MSI specialized equipment to generate an MSI approximation of the reflectance spectra. The parameter(s) of the non-MSI specialized equipment can include parameter(s) of the broadband imaging device and/or parameter(s) of the broadband illumination device.

As part of generating the MSI approximation, certain embodiments use the parameter(s) of the broadband imaging device and parameter(s) of the broadband illumination device to generate a set of spectral base functions that represent a combined operation of the broadband imaging device and the broadband illumination device. For example, the set of spectral base functions may indicate one or more spectral sensitivities of the broadband imaging device across multiple wavelengths of operation of the broadband illumination device. In an exemplary embodiment described below, the set of spectral base functions are generated based on convolving parameter(s) (e.g., spectral emission functions) of the broadband illumination device with parameters (e.g., spectral sensitivity functions) of the broadband imaging device.

Once the set of spectral base functions representing the combined operation of the broadband illumination device and the broadband imaging device are generated, certain embodiments can perform spectral decomposition of the set of spectral base functions to approximate the MSI of reflectance spectra obtained with the target. For example, through spectral decomposition, the reflectance spectra can be assigned into a set of spectral bands, based on eigenvectors and eigenvalues of the spectral base functions. In this manner, embodiments can use parameters of the non-MSI specialized equipment to approximate MSI of reflectance spectra obtained from the target using the non-MSI specialized equipment.

An exemplary ophthalmic system described herein may include a broadband illumination device and a broadband imaging device. The broadband illumination device may include one or more broadband illumination sources, each of which can be independently modulated. For example, the intensity of each broadband illumination source can be independently controlled (over time) relative to the intensity of other broadband illumination sources of the broadband illumination device. In one exemplary embodiment, each broadband illumination source can be independently turned "on" or "off."

The broadband imaging device may include one or more broadband imaging sensors. For example, the broadband imaging device may be a RGB camera. Such a RGB camera may include an imaging sensor configured to capture bands of light in the "red" spectral regions of the visible spectrum, an imaging sensor configured to capture bands of light in the "green" spectral regions of the visible spectrum, and an imaging sensor configured to capture bands of light in the "blue" spectral regions of the visible spectrum.

In certain embodiments, the operation of the broadband illumination device may be synchronized with the operation of the broadband imaging device. For example, the temporal intensity modulation of the broadband illumination source (s) may be synchronized with the scanning of a target (e.g., eye tissue/structure) by the broadband imaging device. In an exemplary embodiment, the turning on/off of the broadband imaging sensors may be synchronized to an image frame of the broadband imaging device. In another exemplary embodiment, the turning on/off of the broadband imaging sensors may be synchronized to the scanning line of the broadband imaging device.

In certain embodiments described in greater detail below, the ophthalmic system may generate MSI information associated with a given target (e.g., eye tissue/structure) based on performing an analytical MSI operation based on (i) spectral information obtained from scanning a target with the broadband imaging device, (ii) parameter(s) of the broadband imaging device, and (iii) parameter(s) of the broadband illumination device. In an exemplary embodiment, the MSI information may include a MSI configuration in which the spectral information is assigned to multiple spectral bands. For example, based on the analytical MSI operation, the ophthalmic system may assign the spectral information into multiple spectral bands, based on the parameter(s) of the broadband imaging device (e.g., spectral sensitivity of the broadband imaging device) and the parameter(s) of the broad illumination device (e.g., spectral emission of the broadband illumination device).

In certain embodiments, the MSI information generated from the analytical MSI operation may be considered approximately equivalent to the "original" spectral information obtained from scanning the target with the broadband imaging device. That is, the MSI information and the original spectral information may produce the same (or similar) sensor output(s) given a same input(s).

In certain embodiments, the MSI information generated from the analytical MSI operation may be used to determine ophthalmic information with respect to a patient's eye. The ophthalmic information can include, but is not limited to, diagnostic, structural, visual, and/or function information associated with the eye. In one exemplary embodiment, the ophthalmic information can include parameters of eye tissues/structures related to a physiological state and/or metabolic state of the ocular tissue. In another exemplary embodiment, the ophthalmic information can include enhanced visualization of eye tissues/structures. As used herein, the terms "information" and "data" may be used interchangeably to refer to qualitative observations and/or quantitative data.

By providing an analytical technique to generate MSI information using non-MSI specialized equipment, embodiments described herein enable ophthalmic systems with existing non-MSI specialized equipment to add functionality for physicians in ophthalmic procedures and to exceed the capability of each individual hardware component by generating MSI information. As such, the embodiments described herein can significantly reduce costs associated with implementing MSI.

As used herein, MSI specialized equipment may refer to a device(s) that is specially designed to be used for MSI applications. Examples of such MSI specialized equipment can include, for example, multi-spectral band illumination sources (e.g., narrowband illumination sources, narrowband filters, etc.), multi-spectral band cameras (e.g., an imaging sensor capable of sensing multiple spectral bands, beyond RGB spectral bands), etc. Additionally, as used herein, non-MSI specialized equipment may refer to a device(s) that is not specially designed to be used for MSI applications. Examples of such non-MSI specialized equipment can include, for example, broadband illumination sources, a broadband illumination source without a narrowband filter, broadband imaging camera (e.g., RGB camera), etc.

FIG. 1 illustrates a system 100 for generating MSI information based on an analytical MSI operation, according to certain embodiments. The system 100 includes an ophthalmic system 130 and an endoilluminator 108 (also referred to as a probe) coupled to the ophthalmic system 130.

The endoilluminator 108 includes a hand-piece 110 coupled to the proximal end of a shaft or "tube" 112, The hand-piece 110 is configured to provide a user (e.g., ophthalmic surgeon) with a graspable portion of the endoilluminator 108 to provide the surgeon a means for manipulating the depth and location of the tube 112 within the eye 120, and for directing the emitted light 150. Tube 112 is a substantially hollow stainless steel shaft or hypodermic tubing, configured to be inserted into the eye 120 via a cannula and sclerotomy 140. In some examples, the tube 112 is fixed coupled to the hand-piece 110. In another example, the tube 112 is rotatable relative to the hand-piece 110. Although the tube 112 is illustrated as a straight shaft, other embodiments include a tube 112 having other shapes. For example, a portion of the tube 112 may be curved to provide light to regions of the eye that would be difficult to illuminate with a straight tube 112. In some embodiments, the endoilluminator 108 and its components are an instrument kit for use in ophthalmic surgery.

The endoilluminator 108 is further configured to house one or more optical fibers configured to direct light out of a distal end of the tube 112. For example, the optical fibers may include an optical fiber array (e.g., a plurality of optical fibers in regular linear arrangement or 2-dimensional pattern arrangement) and/or a multi-core optical fiber (e.g., a single-mode (SM) or multi-mode (MM) fiber with multiple cores). In particular, the hollow portion of the tube 112 includes an interior compartment configured to house the optical fiber (s).

The ophthalmic system 130 includes an illumination device 104, a computing system 144 (also referred to as a controller), and an imaging device 102. The illumination device 104 is generally a broadband illumination device. For example, the illumination device 104 includes one or more (broadband) light sources 160 (also referred to as illumination sources). The light source(s) 160 can generate illumination light beams that may be used during an ophthalmic procedure. For example, the light source(s) 160 may alternatively, sequentially, or simultaneously generate an illumination light beam(s). A user, such as a surgeon or surgical staff member, may control the ophthalmic system 130 (e.g., via a foot switch, voice commands, etc.) to emit the illumination light beam during an ophthalmic procedure, such as vitreoretinal surgery.

The ophthalmic system 130 delivers the illumination light beams from the light source(s) 160 to endoilluminator 108 via optical fiber 152. As shown, the endoilluminator 100's hand-piece 110 is removably coupled to a distal end of optical fiber 152 having a proximal end coupled to illumination device 104. Note that, herein, a distal end of a component refers to the end that is closer to a patient's body, or where the illumination light is emitted out of the illumination device. On the other hand, the proximal end of the component refers to the end that is facing away from the patient's body or in proximity to, for example, the light source.

In operation, a surgeon uses hand-piece 110 to guide tube 112 into a patient's eye 120. Tube 112 is only partly inserted into eye 120 such that the proximal end of tube 112 is disposed outside eye 120. The light source(s) 160 generates an illumination light beam 150, which illuminates the interior of the eye 120, thereby allowing the interior to be viewed with an imaging device, such as imaging device 102.

As noted, in certain embodiments, the light source(s) 160 are broadband light source(s). For example, the light source (s) 160 may include a first broadband light source 160-1 that emits light from the "red" spectral bands of the visible spectrum, a second broadband light source 160-2 that emits light from the "blue" spectral bands of the visible spectrum, and a third broadband light source 160-3 that emits light form the "green" spectral bands of the visible spectrum. Each of the broadband light sources may be a light emitting diode (LED) light source. In certain embodiments, light source(s) 160 is integrated with a console (not shown). In some other embodiments, light source(s) 160 is a stand-alone light source(s).

In certain embodiments described in greater detail below, the intensity of each of the light source(s) 160 may be independently modulated over time. For example, a given light source 160 may be (i) turned "on" (or the intensity of the light source may be increased) or (ii) turned "off" (or the intensity of the light source may be reduced) at any given point in time. As descried below, the temporal modulation of the intensity of each light source 160 may be controlled by the computing system 144, which is described in more detail below.

The system 100 uses optical fiber(s) 152 to transmit illumination light and uses free space transmission to return light. For example, the illumination light beam 150 is directed onto the tissues/structures inside the eye (e.g., retinal surface) from tube 112, and the return light (e.g., at least a portion of the light reflected from the tissues/structures inside the eye) is collected by the imaging device 102. The imaging device 102 is a broadband imaging device (e.g., RGB camera) with one or more imaging sensors 106. Each imaging sensor 106 may be configured to capture light from a particular spectral band of the visible spectrum. Assuming the imaging device 102 is a RGB camera, a (first) imaging sensor 106-1 may be configured to capture spectral bands of light in the "red" spectral regions of the visible spectrum, a (second) imaging sensor 106-2 may be configured to capture spectral bands of light in the "green" spectral regions of the visible spectrum, and a (third) imaging sensor 106-3 may be configured to capture spectral bands of light in the "blue" spectral regions of the visible spectrum.

The imaging device 102 is generally configured to produce (e.g., capture) an image(s) of the targeted tissues/structures inside the eye (e.g., retinal surface) based on the return light. As used herein, the term "return light" may include reflection, scattering, fluorescence, auto fluorescence, Raman spectra, or combinations thereof. In certain embodiments, the operation of the imaging device 102 and the operation of the light source(s) 160 may be synchronized (e.g., via the computing system 144). For example, the computing system 144 may synchronize the generation of illumination light beams (or signals) from the light source(s) 160 with scanning of pixels of the imaging sensor(s) 106.

In an exemplary embodiment, the computing system 144 may synchronize the imaging device 102 and the light source(s) 160, such that the turning on/off of the light source(s) 160 is synchronized to each image frame captured by the imaging device 102. For example, the computing system 144 may control the imaging device 102 to capture three consecutive raw camera images (or readout) of the patient's eye, where only one of the light source(s) 160 is turned on for each image. That is, in this example, each image frame may include return light from a single light source 160.

In another exemplary embodiment, the computing system 144 may synchronize the imaging device 102 and the light source(s) 160, such that the turning on/off of the light source(s) 160 is synchronized to the scanning line (or rolling shutter) of the imaging device 102. In this embodiment, within each image frame captured by the imaging device 102, a given scanning line would include return light from a single light source 160. That is, only one of the light source(s) 160 is turned on for each scanning line of an image frame.

Note that FIG. 1 illustrates a reference example of an ophthalmic system 130 and that, in other embodiments, the ophthalmic system 130 may have different configurations. For example, while FIG. 1 depicts the imaging device 102 and illumination device 104 within the ophthalmic system 130, in some embodiments, the imaging device 102 and/or illumination device 104 may be separate from the ophthalmic system 130. As a reference example, the illumination device 104 may be included within a surgical console and the imaging device 102 may be part of a digital microscope that includes optical components (e.g., an objective) and a digital camera (e.g., RGB camera) to output an image.

Display 142 is coupled to the computing system 144 and is capable of displaying to the surgeon MSI and/or ophthalmic information associated with the eye 120, including MSI information generated by performing an analytical MSI operation with imaging device 102 and illumination device 104. In the illustrated embodiment, display 142 is separate from the imaging device 102 and ophthalmic system 130. In some other embodiments, display 142 is integral with imaging device 102 or ophthalmic system 130. In certain embodiments, display 142 includes an augmented reality display. In certain embodiments, display 142 includes a virtual reality display. In certain embodiments, display 142 includes a three-dimensional display to provide depth information to the surgeon. In certain embodiments, display 142 receives an image(s) captured by the imaging device 102 and presents the image(s) for viewing. In certain embodiments, display 142 receives MSI information from the computing system 144 and presents the MSI information for viewing.

Computing system 144, such as a programmable computer, is generally configured to perform one or more operations described herein for performing an analytical MSI operation. Computing system 144 is coupled to one or more of illumination device 104, imaging device 102, and display 142. For example, computing system 144 may control the operation of ophthalmic system 130 using a direct control of illumination device 104, imaging device 102, and/or display 142 or using indirect control of other controllers associated therewith. In operation, computing system 144 may enable data acquisition and feedback from the respective components to coordinate operation of ophthalmic system 130.

Computing system 144 includes a central processing unit (CPU) 132, a memory 134 that is operable with CPU 132, and circuit(s) 136. Circuit(s) 36 are conventionally coupled to CPU 132 and include cache, clock circuits, input/output subsystems, power supplies, and the like, and combinations thereof coupled to the various components of ophthalmic system 130.

In certain embodiments, CPU 132 is one of any form of general purpose computer processor used in an industrial setting, such as a programmable logic controller (PLC), for controlling various monitoring system components and sub-processors. Memory 134, coupled to CPU 132, is typically one or more of readily available memory, including volatile or non-volatile memory. For example, memory 134 may be a random access memory (RAM), read only memory (ROM), floppy disk drive, hard disk, or any other form of digital storage, local or remote.

Herein, memory 134 stores instructions, that when executed by CPU 132, facilitates the operation of ophthalmic system 130. The instructions in memory 134 are in the form of a program product such as a program that implements the methods of the present disclosure (e.g., middleware application, equipment software application, etc.). As shown, the memory 134 includes a MSI component 138 (e.g., software component), which is generally configured to perform an analytical MSI operation to generate MSI information. The MSI component 138 is described in greater detail below. Note that methods disclosed herein may be carried out using one or more of the ophthalmic system embodiments provided, and thus, ophthalmic system 130 is described in the following examples for illustrative purposes only.

Figure 2:
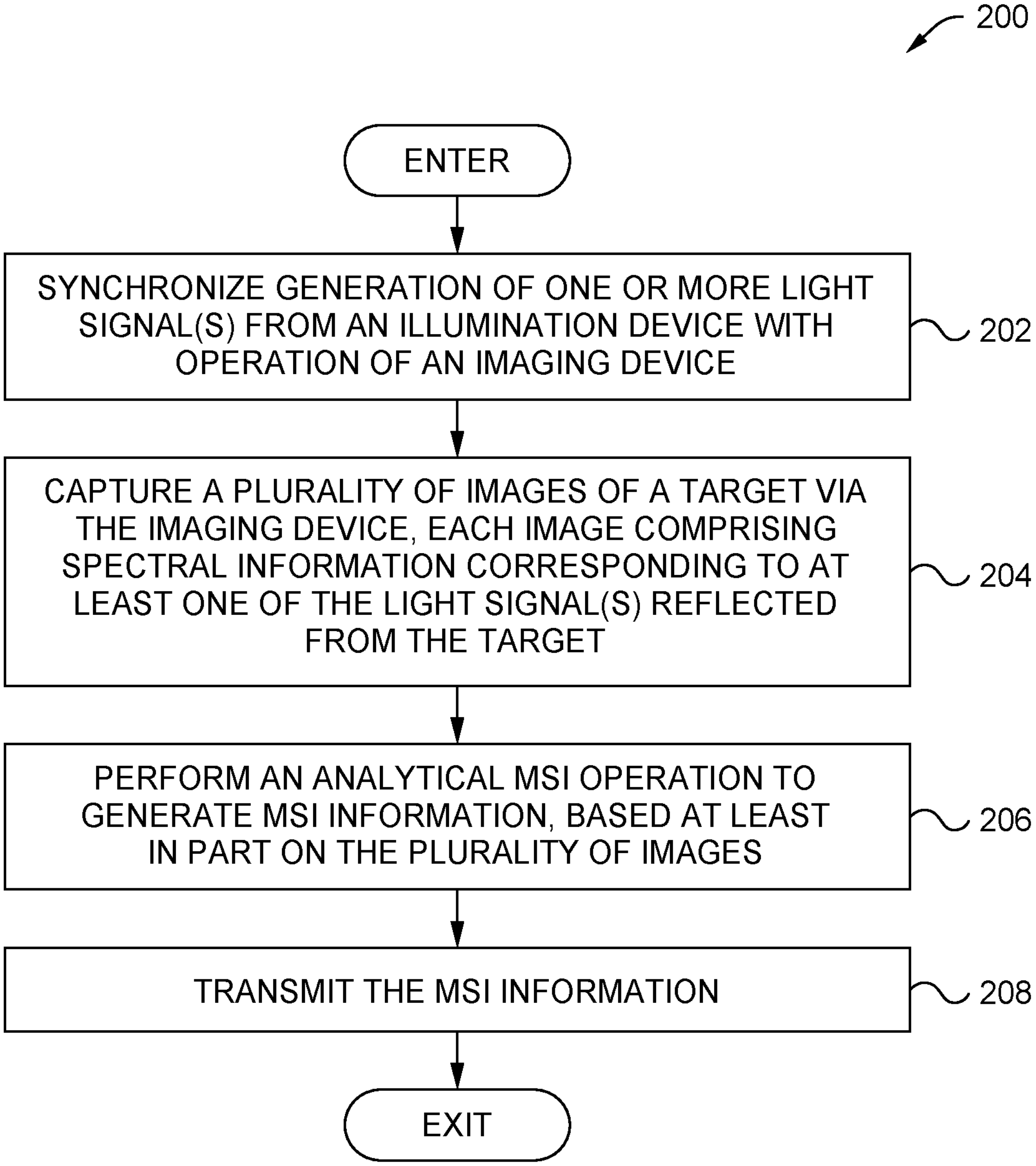
FIG. 2 is a flowchart of a method for generating MSI information based on an analytical MSI operation, according to certain embodiments.

FIG. 2 is a flowchart of a method 200 for generating MSI information based on an analytical MSI operation, according to one embodiment. The method 200 may be performed by one or more components of a system (e.g., system 100).

Method 200 enters at block 202, where the system synchronizes generation of one or more light signals from an illumination device (e.g., illumination device 104) with operation of an imaging device (e.g., imaging device 102). As noted, in certain embodiments, the temporal modulation of the intensity of the light source(s) (e.g., light sources 160) within the illumination device may be synchronized with the captured image frame(s) of the imaging device or with the scanning line(s) within the captured image frame of the imaging device.

Figure 3:
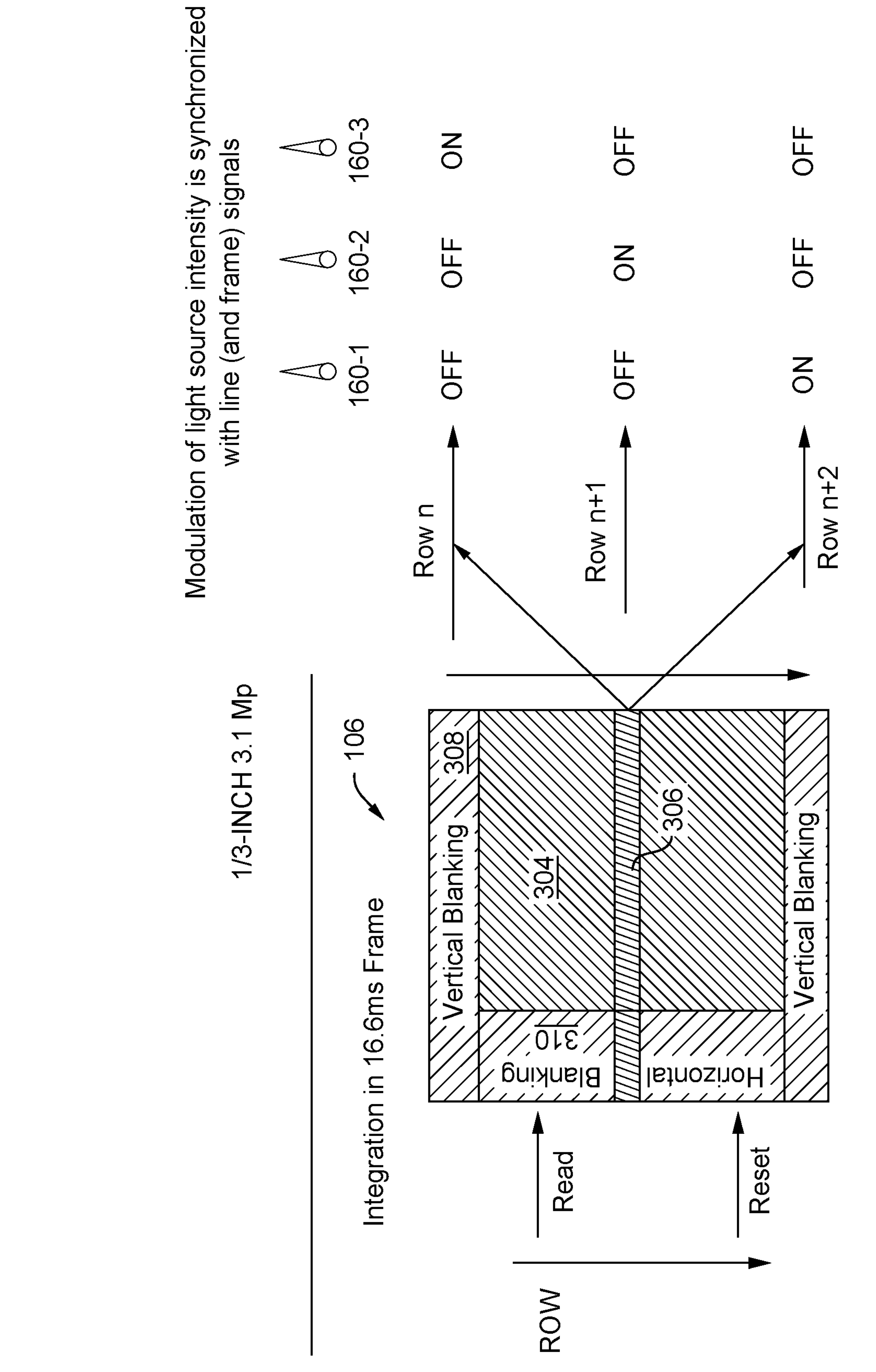
FIG. 3 illustrates an example of temporal intensity modulation of an illumination device, according to certain embodiments.

By way of example, briefly referring to FIG. 3, this figure illustrates an example of temporal modulation of the intensity of multiple light sources 160, according to certain embodiments. In the depicted embodiment, the imaging sensor 106 is a ⅓ inch 3.1 Megapixel (Mp) CMOS digital image sensor with an active pixel array 304 (e.g., pixel array of 2048 (H)×1536 (V)). The pixel array may include RGB pixels. Note, however, that the pixel array depicted in FIG. 3 is merely an example and that pixel arrays of other configurations/sizes consistent with the functionality described herein can be used.

The pixel array 304 has a coarse integration time defined by the number of row periods ($T_{ROW}$) between a row's reset and the row's read. The row period ($T_{ROW}$) is defined as the time between row read operations. The pixel array 304 includes vertical blanking signals 308 and horizontal blanking signals 310. Each vertical blanking signal 308 is configured as a blanking row (of the pixel array 304) to indicate when a new image frame is starting. The horizontal blanking signals 310 are configured as a blanking column (across one or more rows) to indicate when a new scan line is starting. Thus, in the depicted example, the imaging sensor 106 may start a frame readout beginning with a vertical blanking row (e.g., vertical blanking signal 308) followed by one or more active rows (between the vertical blanking rows 308). Each active row of the frame readout may begin with a horizontal blanking signal 310. That is, the imaging sensor 106 may read the first vertical blanking row at the beginning of the frame period and the last active row at the end of the row period. Configuring pixel array 304 in the manner described above is beneficial because it allows the imaging sensor 106 to capture continuous video and single frames and to operate in different modes, including, for example, a high dynamic range mode of operation, where the imaging sensor 106 can capture a wide range of illumination with intensities varying over 100 dB range or more.

In certain embodiments, the modulation of the intensity of the light sources 160 is synchronized with the line (and frame) signals (e.g., vertical blanking signal 308 and horizontal blanking signal 310) of the imaging sensor 302. For example, the intensity of a light source 160 may be controlled through multiplexing, in-sync with vertical blanking signals 308 and horizontal blanking signals 310. As noted, in an exemplary embodiment, the modulation approach may involve implementing an "on" and "off" for a particular light source 160 within a particular row. The benefit of multiplexing within a single image frame is that the spectral information in a local region under different intensity combinations of light can be compared, without the need to correct eye motion. The rapid modulation of the light intensities may also minimally interrupt visualization during ophthalmic surgical procedures.

As shown in FIG. 3, the modulation of the intensity of the light sources 160 is controlled such that only one of the light sources 160 is turned "on" for the duration of a respective scanning line 306. For example, when scanning line 306 is on row "n," light source 160-1 is turned "off," light source 160-2 is turned "off," and light source 160-3 is turned "on"; when scanning line 306 is on row "n+1," light source 160-1 is turned "off," light source 160-2 is turned "on," and light source 160-3 is turned "off"; when scanning line 306 is on row "n+2," light source 160-1 is turned "on," light source 160-2 is turned "off," and light source 160-3 is turned "off"; and so on. By modulating the intensity of the light source(s) 160 in this manner, the ophthalmic system 130 can differentially sample spectral bands in the return light from the patient's eye.

In certain embodiments, the intensity of the light sources 160 can be modulated according to the percentage of "off" time. Doing this can maintain relative constant average illumination and, in turn, minimize visual flickering in the visual output. Additionally, in certain embodiments, the modulation of the intensity of the light sources 160 can be confined to a target region of the frame, such as the center of the frame.

Referring back to FIG. 2, at block 204, the system captures a plurality of images of a target (e.g., eye tissue/structure) via the imaging device. Each image includes spectral information corresponding to at least one of the light signal(s) reflected from the target. For example, for a given target (or feature) in a patient's eye, the light signal(s) reflected from the target and captured by the imaging device may be described using the following Equation (1). (note that, for the sake of clarity, the equations below are described for 3 light sources and 3 types of image sensors; however, the equations below can be used for any number of light sources and/or any number of image sensors):

$$I_{Sensor} = \sum_{\lambda} \text{Sensor}(\lambda) \cdot \text{Illumination}(\lambda) \cdot \text{Reflectance}(\lambda) \tag{1}$$

where Reflectance (λ) is the spectral reflectance of the target across wavelength (λ), the spectral sensitivities of the imaging sensors are [$\text{Sensor}_R$,$\text{Sensor}_G$,$\text{Sensor}_B$], and the spectral emissions of the illumination device 104 are [$\text{Illumination}_1$, $\text{Illumination}_2$,$\text{Illumination}_3$] for the three independently modulated primary light sources 160.

In certain embodiments, with the temporal intensity modulation approach described herein (e.g., where only one primary light source in the illumination device is turned on at a time), the readout from the imaging device may be represented using the following Equation (2), which can be expressed in matrix form with Equation (3). Note for the sake of clarity, the summation symbol is omitted from Equation (2).

$$\begin{bmatrix} I_{R-1} \\ I_{G-1} \\ I_{B-1} \\ I_{R-2} \\ I_{G-2} \\ I_{B-2} \\ I_{R-3} \\ I_{G-3} \\ I_{B-3} \end{bmatrix} = \begin{bmatrix} \text{Sensor}_R(\lambda) \cdot \text{Illumination}_1(\lambda) \cdot \text{Reflectance}(\lambda) \\ \text{Sensor}_G(\lambda) \cdot \text{Illumination}_1(\lambda) \cdot \text{Reflectance}(\lambda) \\ \text{Sensor}_B(\lambda) \cdot \text{Illumination}_1(\lambda) \cdot \text{Reflectance}(\lambda) \\ \cdots \\ \cdots \\ \cdots \\ \cdots \\ \text{Sensor}_G(\lambda) \cdot \text{Illumination}_3(\lambda) \cdot \text{Reflectance}(\lambda) \\ \text{Sensor}_B(\lambda) \cdot \text{Illumination}_3(\lambda) \cdot \text{Reflectance}(\lambda) \end{bmatrix} \tag{2}$$

$$I_{camera} = \text{BaseMatrix} \times \text{Reflectance} \tag{3}$$

where $I_{camera}$ is represented using Equation (4) and BaseMatrix is represented using Equation (5):

$$I_{camera} = \begin{bmatrix} I_{R-1} \\ I_{G-1} \\ I_{B-1} \\ I_{R-2} \\ I_{G-2} \\ I_{B-2} \\ I_{R-3} \\ I_{G-3} \\ I_{B-3} \end{bmatrix} \tag{4}$$

$$BaseMatrix = \begin{bmatrix} BaseFunction_{R-1} \\ BaseFunction_{G-1} \\ BaseFunction_{B-1} \\ \cdots \\ \cdots \\ \cdots \\ \cdots \\ BaseFunction_{G-3} \\ BaseFunction_{B-3} \end{bmatrix} = \begin{bmatrix} Sensor_R(\lambda) \cdot Illumination_1(\lambda) \\ Sensor_G(\lambda) \cdot Illumination_1(\lambda) \\ Sensor_B(\lambda) \cdot Illumination_1(\lambda) \\ \cdots \\ \cdots \\ \cdots \\ \cdots \\ Sensor_G(\lambda) \cdot Illumination_3(\lambda) \\ Sensor_B(\lambda) \cdot Illumination_3(\lambda) \end{bmatrix} \tag{5}$$

At block 206, the system performs an analytical MSI operation to generate MSI information, based at least in part on the plurality of images. In certain embodiments, the system may generate the MSI information based on the spectral information corresponding to at least one of the light signals reflected from the target, parameters of the imaging device (e.g., spectral sensitivities of the imaging sensors), and parameters of the illumination device (e.g., spectral emissions of the illumination device). In certain embodiments, the parameters of the imaging device and/or the parameters of the illumination device may be preconfigured parameters associated with the imaging system.

In certain embodiments, the MSI information generated from the analytical MSI operation may include a MSI configuration of the target surface reflectance. For example, the MSI configuration may assign (or express) the target surface reflectance into a multiple band approximation, an example of which is shown in (6):

$$SpectralBand = \begin{bmatrix} Band_1(\lambda) = 1 & 445 \le \lambda \le 490\text{ nm} \\ Band_2(\lambda) = 1 & 490 \le \lambda \le 520\text{ nm} \\ Band_3(\lambda) = 1 & 520 \le \lambda \le 580\text{ nm} \\ Band_4(\lambda) = 1 & 580 \le \lambda \le 610\text{ nm} \\ Band_5(\lambda) = 1 & 610 \le \lambda \le 665\text{ nm} \end{bmatrix} \tag{6}$$

Given a multiple band approximation (e.g., SpectralBand), the surface reflectance may be approximated using Equation (7):

$$Ref\widehat{lectance} = SpectraBand^T \times \begin{bmatrix} I_{MSI-band1} \\ I_{MSI-band2} \\ I_{MSI-band3} \\ I_{MSI-band4} \\ I_{MSI-band5} \end{bmatrix} \tag{7}$$

(Note, $SpectraBand^T$ is the transpose of matrix SpectraBand).

In certain embodiments, using the approximation in (7), the following Equation (8) may be derived and used for the analytical MSI operation:

$$I_{camera} = BaseMatrix \times SpectraBand^T \times I_{MSI} \tag{8}$$

where $$I_{MSI} = \begin{bmatrix} I_{MSI\text{-}band1} \\ I_{MSI\text{-}band2} \\ I_{MSI\text{-}band3} \\ I_{MSI\text{-}band4} \\ I_{MSI\text{-}band5} \end{bmatrix}$$

is the intensity within each MSI spectral band.

In certain embodiments, the spectral bands for analytical MSI (e.g., $I_{MSI}$) may be chosen in order to make BaseMatrix×SpectraBand$^T$ invertible. For example, making BaseMatrix×SpectraBand$^T$ invertible allows for the conversion of an RGB image captured from the imaging device to multiple MSI images to be fully invertible. In such cases where the conversion of an RGB image captured from the imaging device to multiple MSI images is fully invertible, the MSI information generated from the analytical MSI operation can be used to visually enhance certain features of the patient's eye. For example, an image enhancement may be implemented in the multispectral domain for one spectral band (e.g., a particular "blue" signal enhancement) using spectral information obtained by scanning multiple lines in a frame (or by scanning multiple frames) with different modulation of the intensities of the light sources. The image enhancement may then be converted back to a RGB image to enhance visualization of a procedure (e.g., blue light in vitrectomy).

Additionally, in certain embodiments, as part of analytical MSI, a singular value decomposition operation of the BaseMatrix may be performed. The singular value decomposition operation may be performed on the BaseMatrix to determine a number of bands of the MSI information. For example, the number of bands of the MSI information may be set equal to the column space of the BaseMatrix (determined from the singular value decomposition operation). Because the column space of the BaseMatrix may have a number of singular values (for a first set of column vectors) that are significantly larger than the rest of the singular values (of a second set of column vectors), the analytical MSI may be defined to have a number of bands equal to the number of the first set of column vectors (e.g., the column space of the BaseMatrix). This number of bands may then have cut points defined to match the spectral shape of the first set of column vectors. Note the analytical MSI operation is described in more detail below with respect to FIG. 4.

At block 208, the system transmits the MSI information to a computing device for display and/or further processing. As noted, in certain embodiments, the MSI information may be used to enable more anatomical and functional assessment of an eye condition. For example, the MSI information may be used to identify the pathological state of ocular tissue using spectral characteristics and differentiate it from healthy ocular tissue, to infer the metabolic state of the retina using the oxygen content in the blood, given that the spectral reflectance of vessels changes with the amount of oxygen level, enhance visualization of ocular structures, etc.

Figure 4:
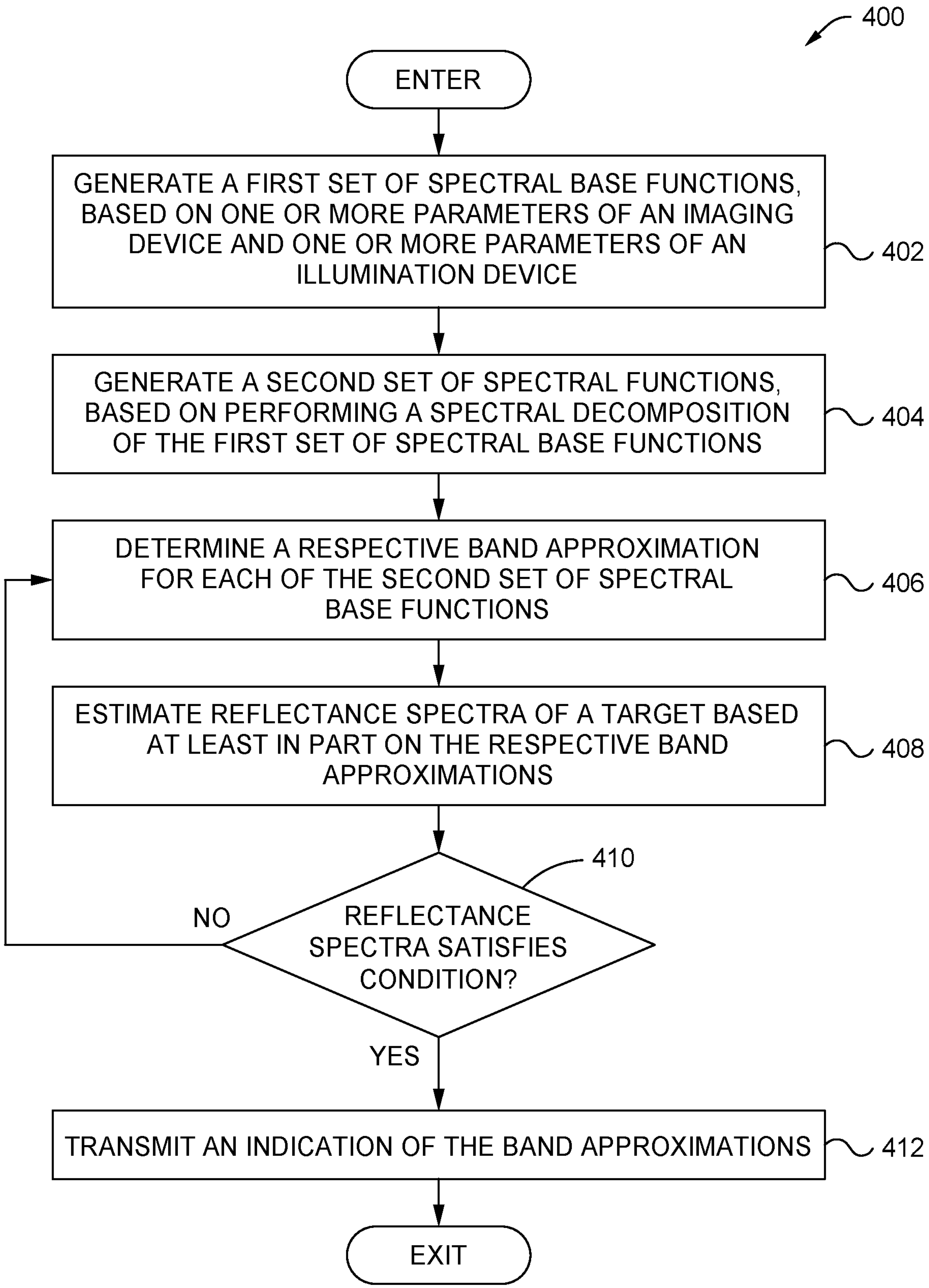
FIG. 4 is a flowchart of a method for performing an analytical MSI operation, according to certain embodiments.

FIG. 4 is a flowchart of a method 400 for performing an analytical MSI operation, according to one embodiment. The method 400 may be performed by one or more components of a system (e.g., system 100). In certain embodiments, the method 400 may be performed to implement the operations in block 206 of the method 200 illustrated in FIG. 2.

Method 400 enters at block 402, where the system generates a first set of spectral base functions (e.g., BaseFunctions in Equation (5)), based on one or more parameters of an imaging device (e.g., imaging device 102) and one or more parameters of an illumination device (e.g., illumination device 104). As noted, the parameter(s) of the imaging device may include spectral sensitivities of the imaging sensors (e.g., imaging sensors 106) of the imaging device. The parameter(s) of the illumination device may include spectral emissions of the light sources (e.g., light sources 160) of the illumination device.

Figure 5A:
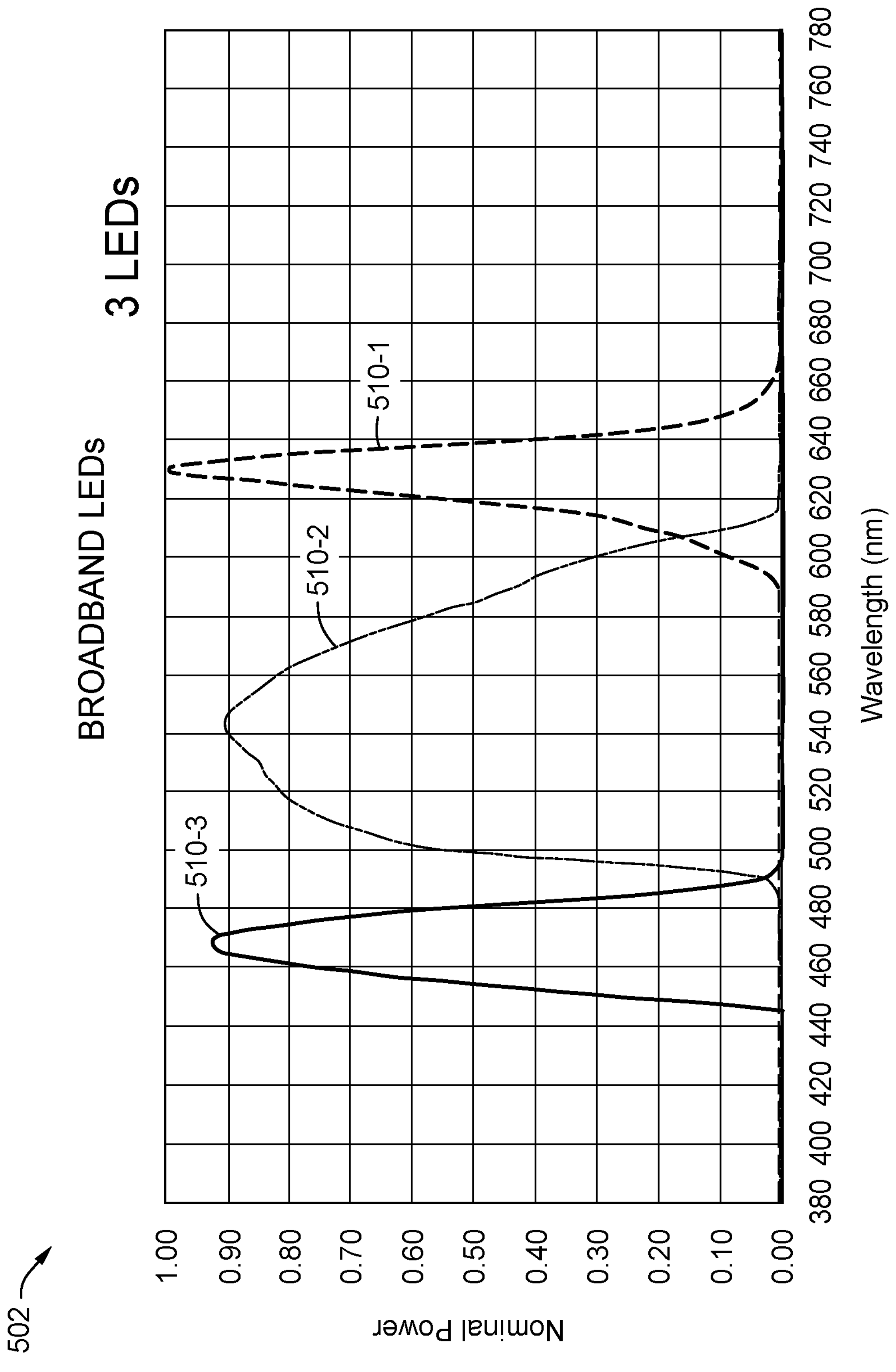
FIG. 5A illustrates a graph of spectral emission functions, according to certain embodiments.
Figure 5B:
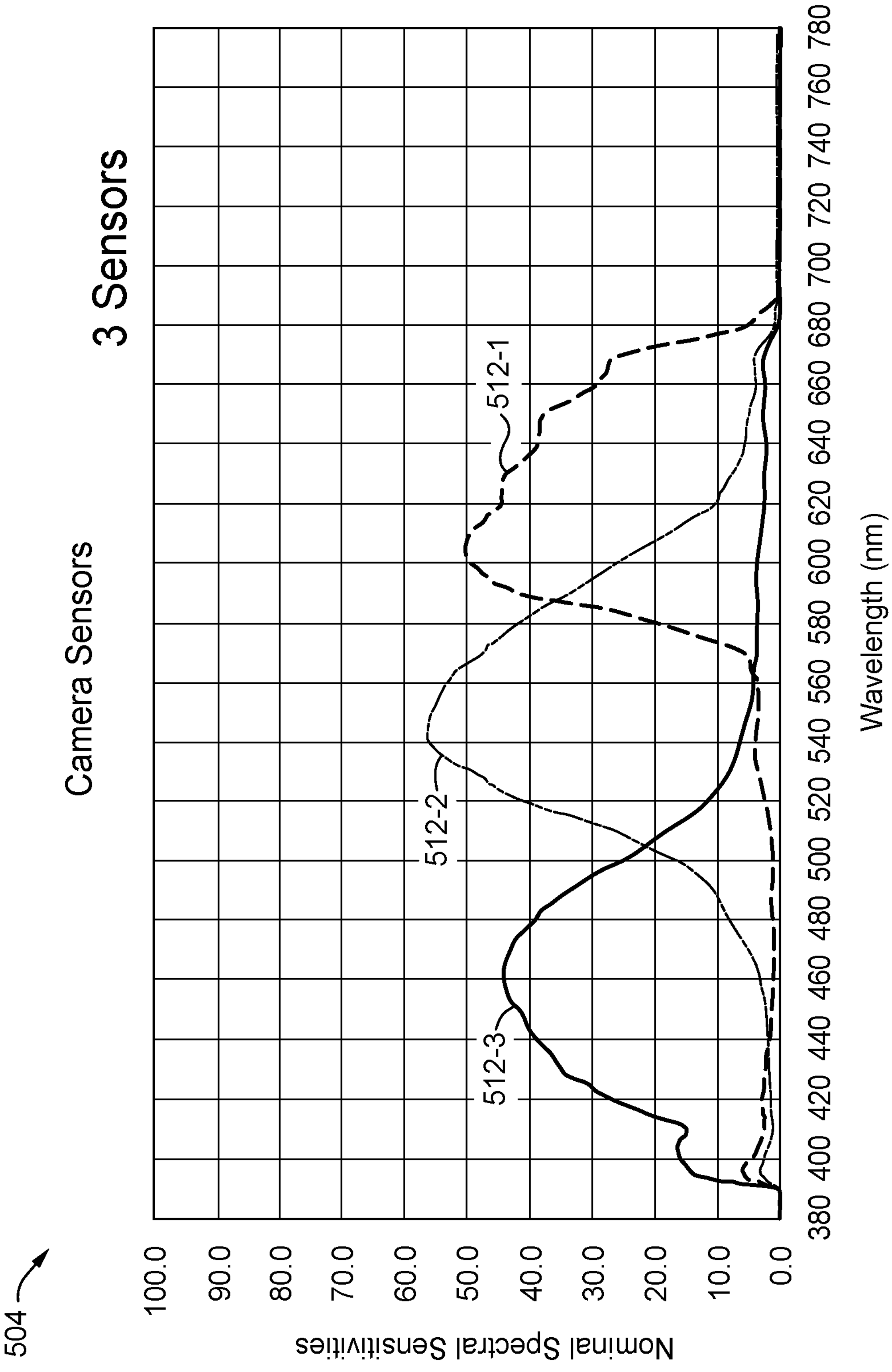
FIG. 5B illustrates a graph of spectral sensitivity functions, according to certain embodiments.
Figure 5C:
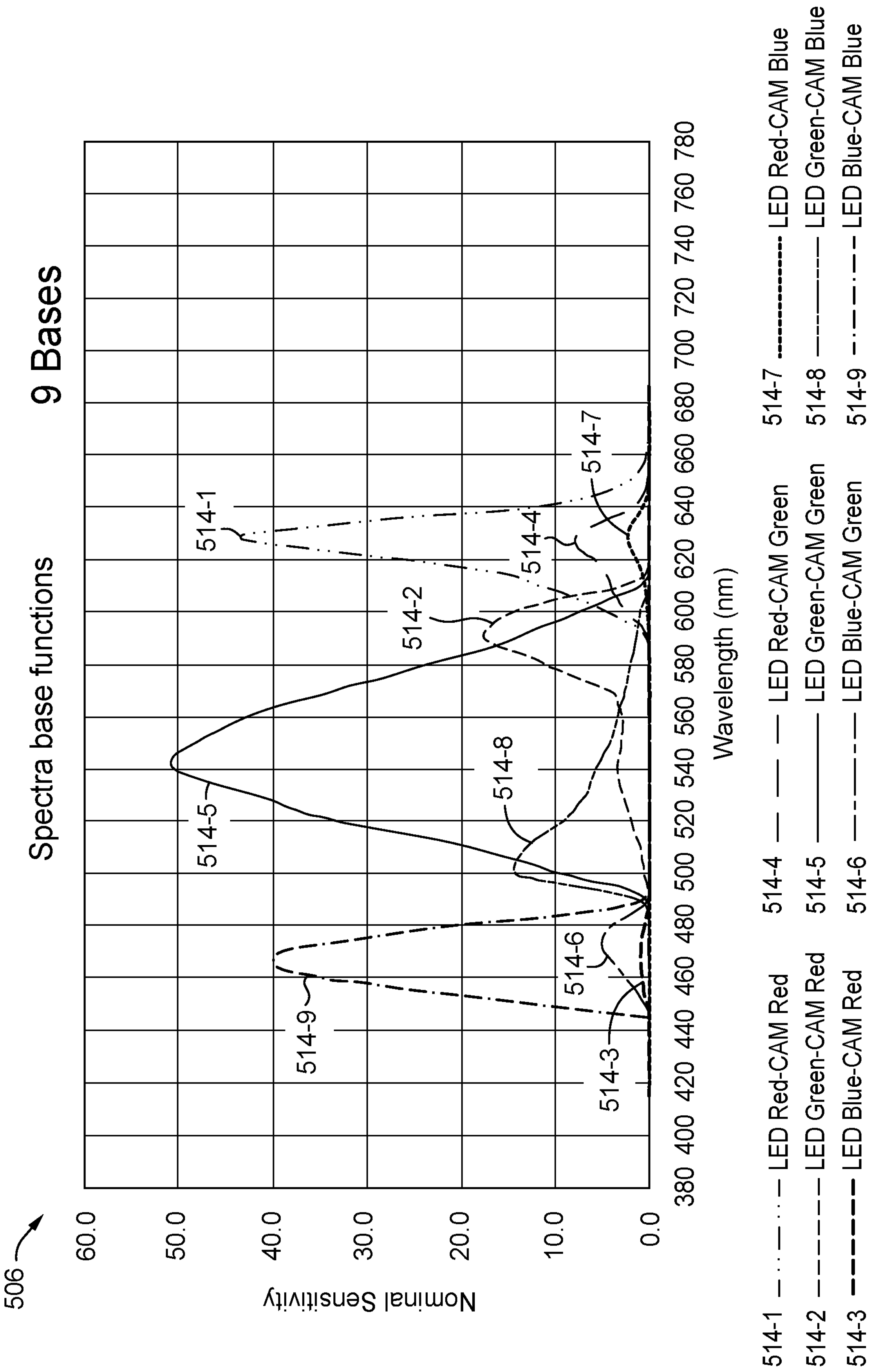
FIG. 5C illustrates a graph of spectral base functions generated as part of an analytical MSI operation, according to certain embodiments.

In certain embodiments, the first set of spectral base functions may be generated by performing a convolution of (i) the spectral sensitivities of the imaging sensors and (ii) the spectral emissions of the light sources. Referring to FIGS. 5A-5C, by way of example, an exemplary convolution of 3 spectral emission functions 510 1-3 in graph 502 of FIG. 5A and 3 spectral sensitivity functions 512 1-3 in graph 504 of FIG. 5B is illustrated. In graph 502, function 510-1 (e.g., $Illumination_1(\lambda)$ in Equation (5)) is the spectral emission of a "red" broadband light source, function 510-2 (e.g., $Illumination_2(\lambda)$ in Equation (5)) is the spectral emission of a "green" broadband light source, and function 510-3 (e.g., $Illumination_3(\lambda)$ in Equation (5)) is the spectral emission of a "blue" broadband light source. In graph 504, function 512-1 (e.g., $Sensor_R(\lambda)$ in Equation (5)) is the spectral sensitivity of a "red" imaging sensor, function 512-2 (e.g., $Sensor_G(\lambda)$ in Equation (5)) is the spectral sensitivity of a "green" imaging sensor, and function 512-3 ($Sensor_B(\lambda)$ in Equation (5)) is the spectral sensitivity of a "blue" imaging sensor.

In certain embodiments, the set of base functions may be generated by convolving each function 510 with each function 512. As shown in graph 506 of FIG. 5C, for example, base function 514-1 is generated based on convolving function 510-1 and function 512-1, base function 514-2 is generated based on convolving function 510-2 and function 512-1, base function 514-3 is generated based on convolving function 510-3 and function 512-1, base function 514-4 is generated based on convolving function 510-1 and function 512-2, base function 514-5 is generated based on convolving function 510-2 and function 512-2, base function 514-6 is generated based on convolving function 510-3 and function 512-2, base function 514-7 is generated based on convolving function 510-1 and function 512-3, base function 514-8 is generated based on convolving function 510-2 and function 512-3, and base function 514-9 is generated based on convolving function 510-3 and function 512-3.

Figure 5D:
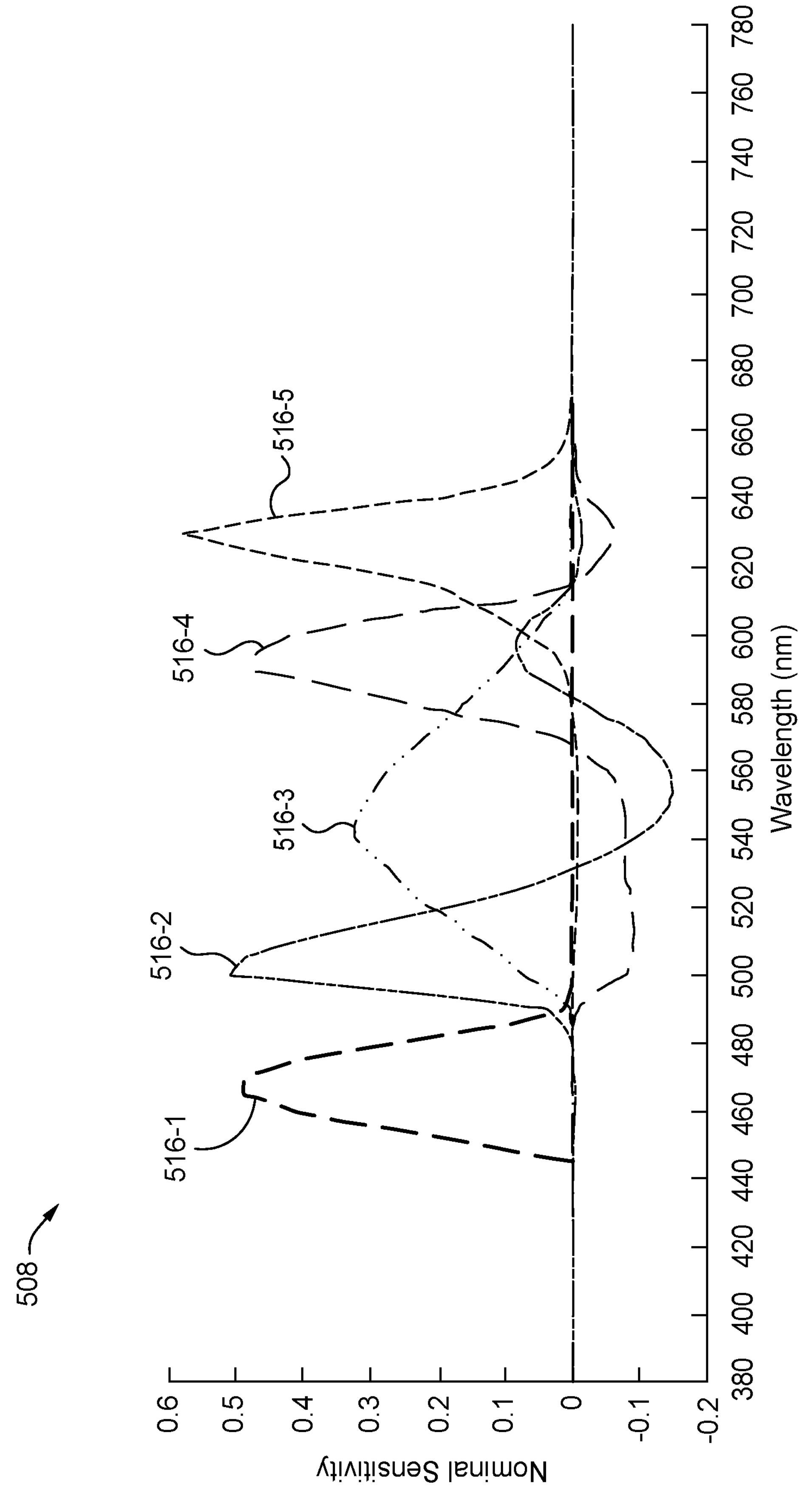
FIG. 5D illustrates an example of a reduced set of spectral base functions generated as part of an analytical MSI operation, according to certain embodiments.

Referring back to FIG. 4, at block 404, the system generates a second set of spectral base functions, based on performing a spectral decomposition of the first set of spectral base functions. In certain embodiments, a number of spectral base functions in the second set of spectral base functions may be smaller than a number of spectral base functions in the first set of spectral base functions. Referring to FIG. 5D, by way of example, an exemplary spectral decomposition of a set of base functions is illustrated. In the depicted embodiment, the set of base functions in graph 506 of FIG. 5C is reduced to the set of base functions in graph 508 in FIG. 5D, which includes spectral base functions 516 1-5. In this example, the set of base functions is reduced from 9 to 5, based on the eigenvalues of the 9 base functions. Note that graph 508 illustrates the column space of the spectral base functions from graph 506.

Continuing with FIG. 4, at block 406, the system determines a respective band approximation for each of the second set of spectral base functions. For example, the system may determine a multiple band approximation to use as $SpectraBand^T$ in Equation (7). At block 408, the system estimates reflectance spectra of a target based at least in part on the respective band approximations. For example, the operations in block 408 may be performed using Equation (7).

Figure 6A:
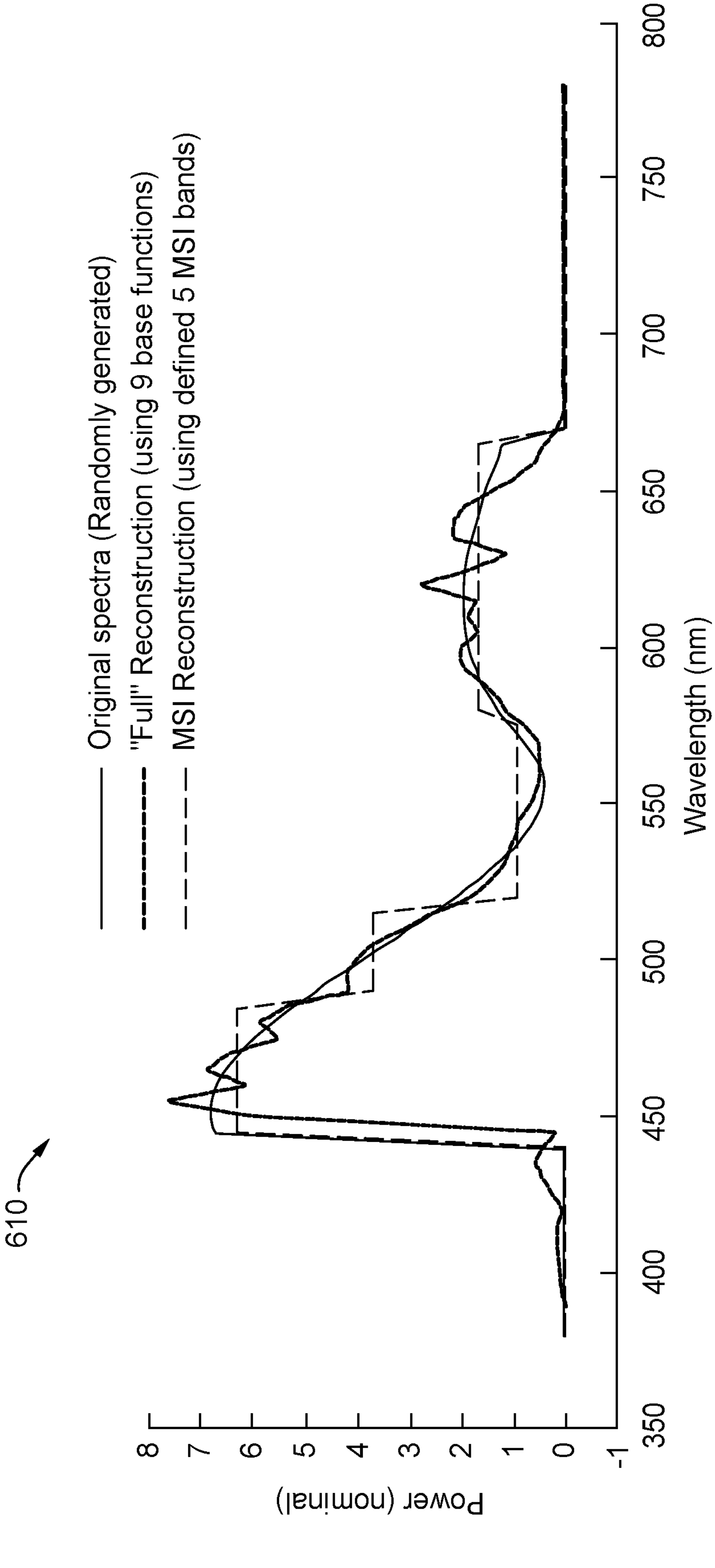
FIGS. 6A-6B illustrate graphs of example reconstructions of original spectra using MSI information generated as part of an analytical MSI operation, according to certain embodiments.
Figure 6B:
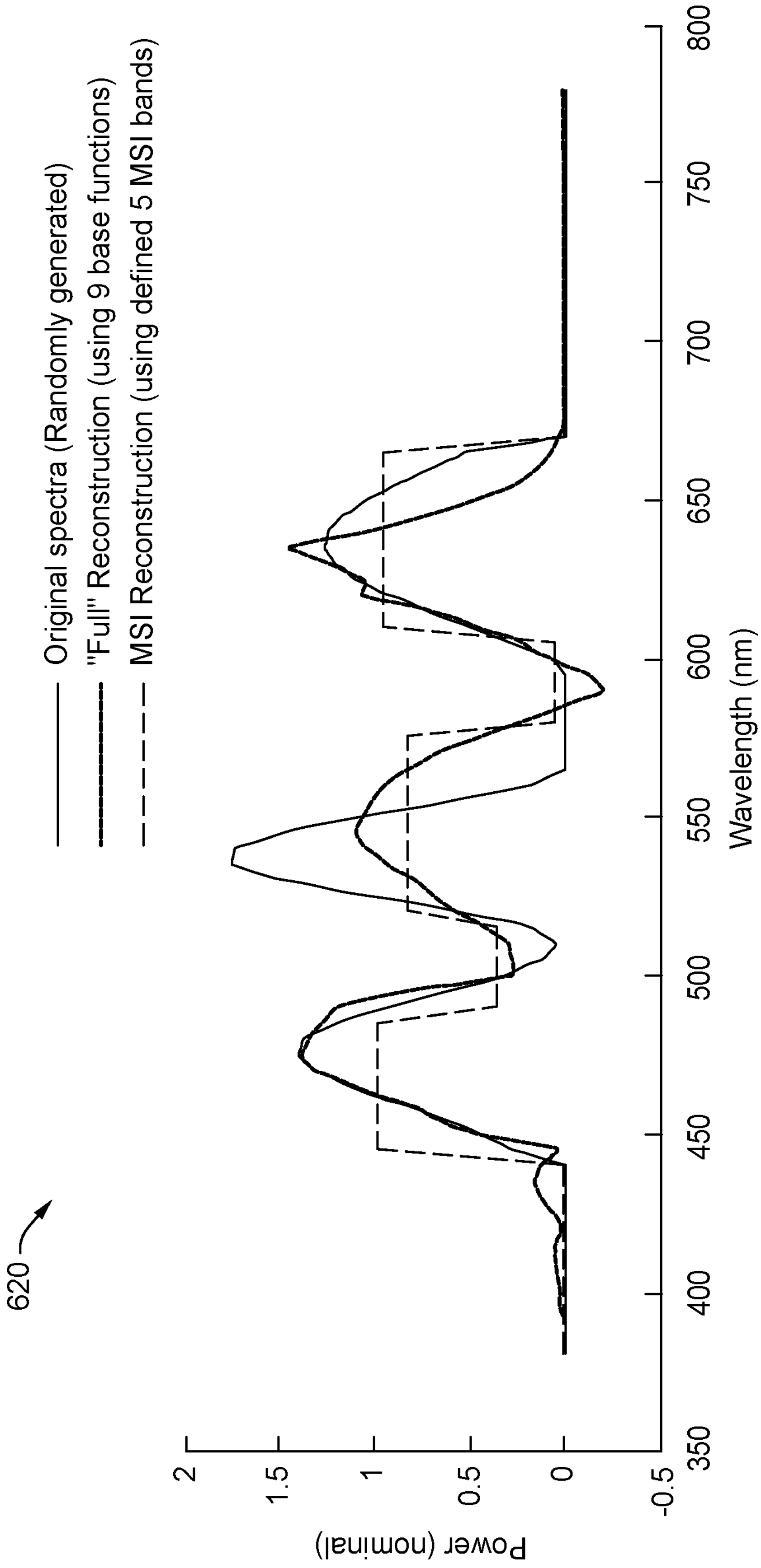

At block 410, the system determines whether the reflectance spectra satisfies a predetermined condition. For example, in certain embodiments, the reflectance spectra determined in block 406 (e.g., MSI approximated reflectance spectra) should be equivalent to the original reflectance spectra (e.g., the spectrum of the return light from the targeted features), with a certain amount of tolerance for reconstruction error. For example, FIGS. 6A and 6B illustrate graphs 610 and 620, respectively, of a MSI reconstruction of original spectra (e.g., using a defined set of MSI bands) and a full reconstruction of original spectra (e.g. using a full set of spectral base functions).

Figure 5E:
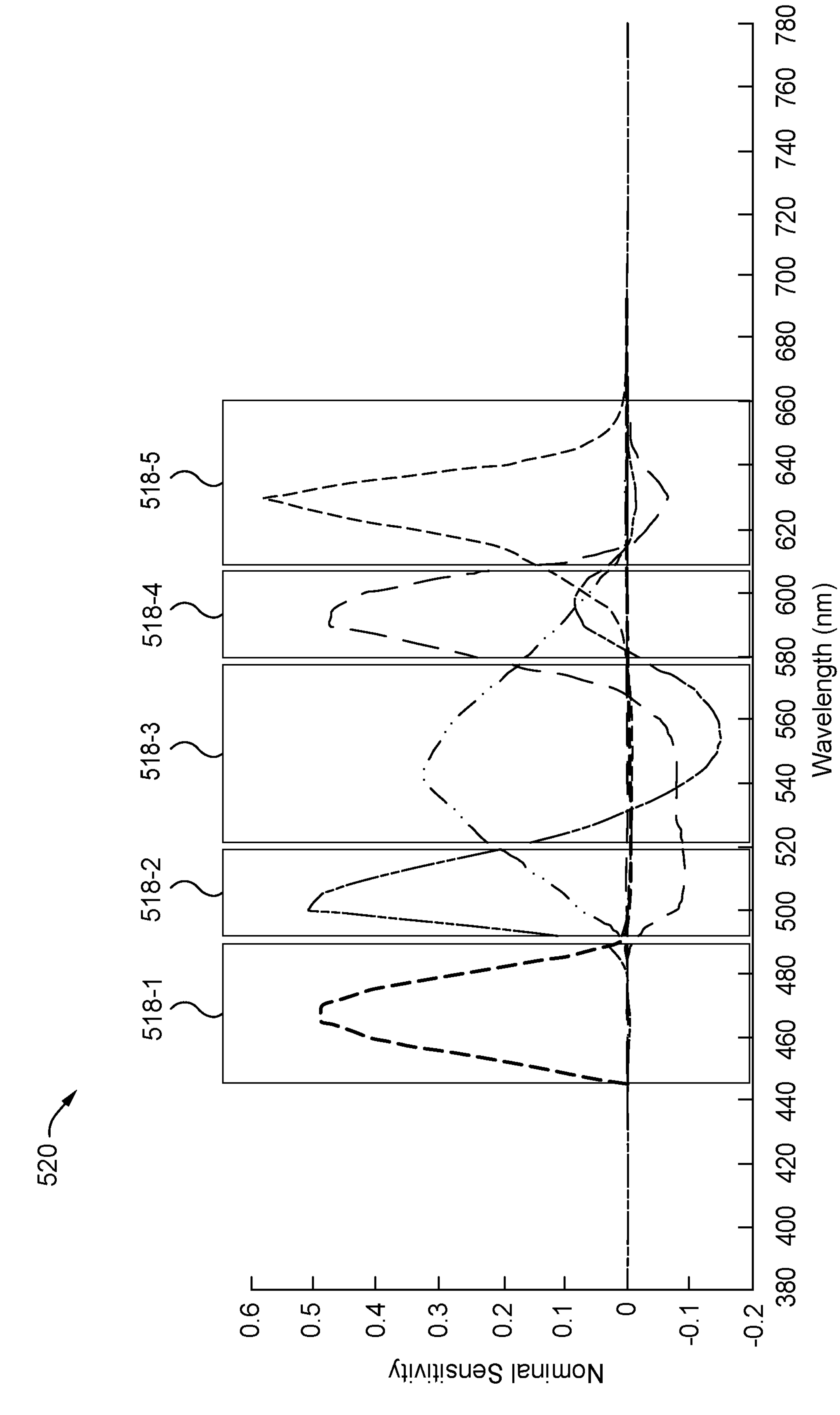
FIG. 5E illustrates an example of band approximations for the reduced set of spectral base functions in FIG. 5D, according to certain embodiments.

Referring back to FIG. 4, if the difference between the reflectance spectra and the original reflectance spectra is greater than a threshold (or is outside of a threshold range), then the system may proceed to block 406 to determine another respective band approximation for each of the second set of spectral base functions. On the other hand, if the reflectance determined in block 406 is equivalent to the original reflectance spectra, then the system transmits an indication of the band approximations (block 412) to a computing system for display and/or further processing. In certain embodiments, the system may also transmit an indication of the reflectance spectra to the computing system. In certain embodiments, instead of transmitting the indication of the band approximations at block 412, the system itself may display the band approximations and/or perform further processing of the band approximations An example of band approximations is shown in graph 520 of FIG. 5E. As shown, the graph 520 includes a first approximation 518-1 of the band for spectral base function 516-1, a second approximation 518-2 of the band for spectral base function 516-2, a third approximation 518-3 of the band for spectral base function 516-3, a fourth approximation 518-4 of the band for spectral base function 516-4, and a fifth approximation 518-5 of the band for spectral base function 516-5. In FIG. 5E, the cut points of each respective band approximation may be aligned with the waveform of its respective spectral base function.

Figure 7:
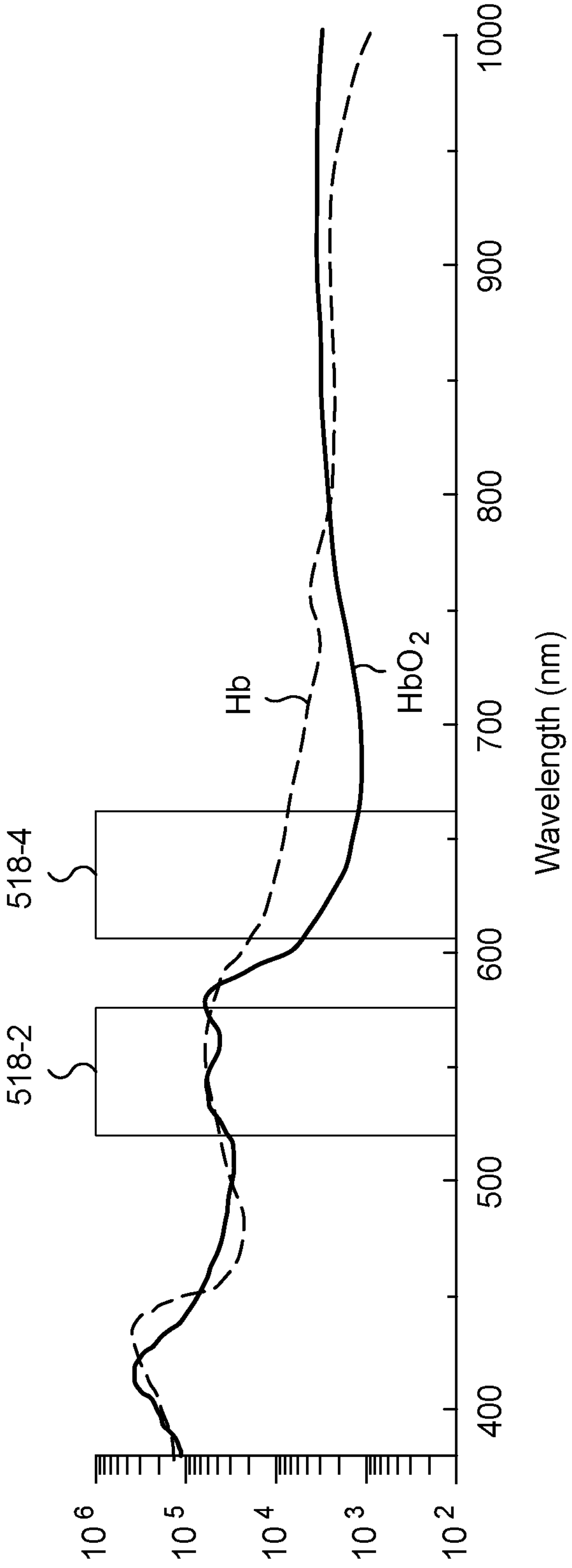
FIG. 7 illustrates an example of using MSI information to determine ophthalmic information associated with a patient's eye, according to certain embodiments.
Figure 8:
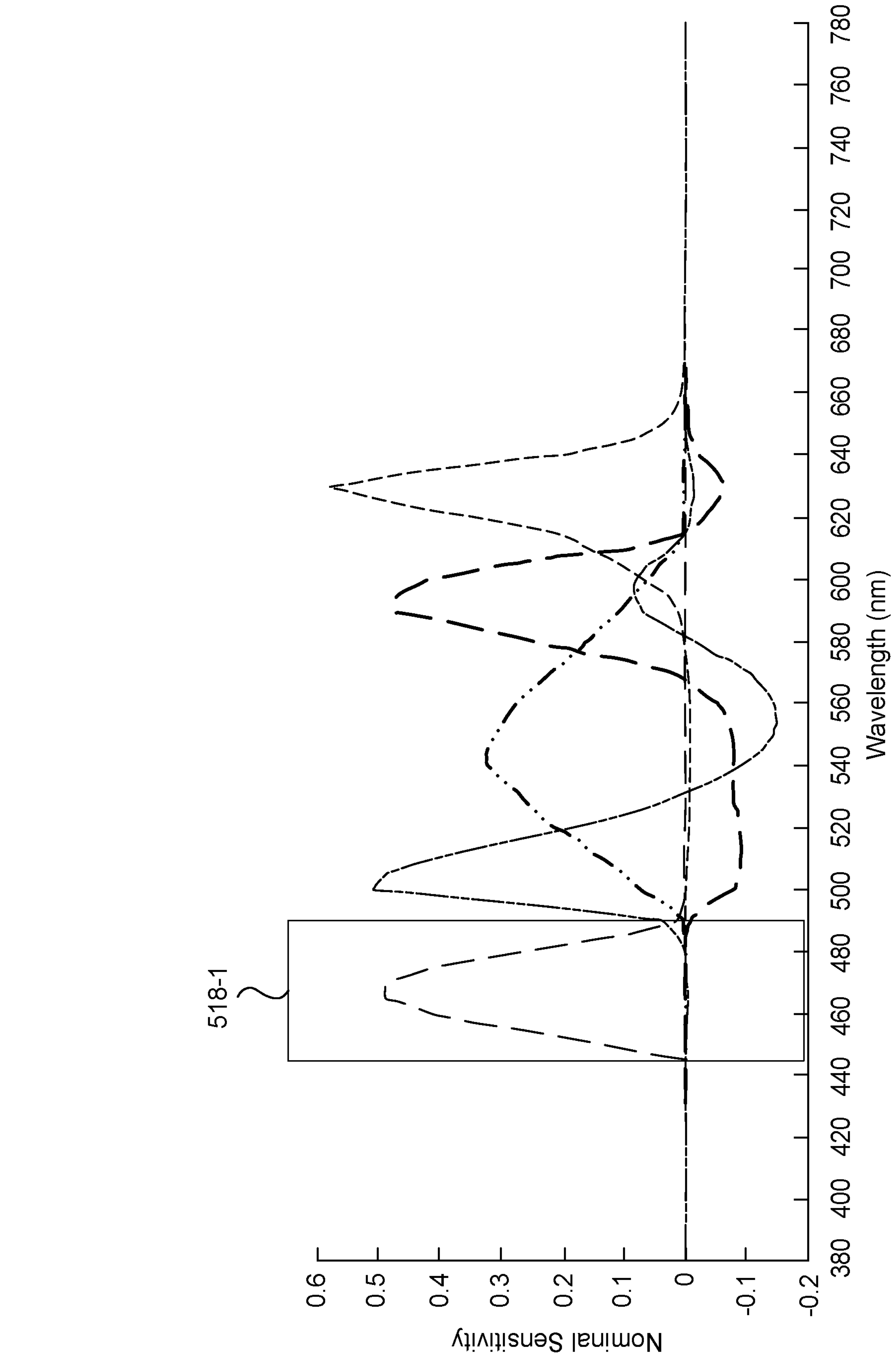
FIG. 8 illustrates an example of using MSI information to visually enhance a feature(s) of the patient's eye, according to certain embodiments.

As noted, in certain embodiments, the MSI information generated using the analytical MSI technique described herein can be used to determine ophthalmic information. By way of example, FIG. 7 illustrates an example of using MSI information to determine an oximetry of the eye, according to certain embodiments. As shown, assuming the MSI information includes 5 spectral bands derived from the column space of the 9 spectral base functions, the oximetry may be calculated using two of the 5 spectral bands. In another example, FIG. 8 illustrates using MSI information to perform image enhancement. In this example, the image enhancement is performed in the multispectral domain and includes a visualization of a subset of the MSI information (e.g., band approximation 518-1 is enhanced relative to the other band approximations 518 2-4).

In summary, embodiments of the present disclosure enable the generation of MSI information without the use of MSI-specialized equipment, based on performing an analytical MSI technique using non-MSI specialized equipment, such as broadband illumination device and broadband imaging device. Ophthalmic systems and/or methods described herein are particularly advantageous for significantly reducing the cost associated with implementing MSI.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a c c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. A system comprising:

an illumination device comprising a plurality of broadband illumination sources;

a broadband imaging device comprising a plurality of imaging sensors;

a memory comprising executable instructions; and a processor in data communication with the memory and configured to execute the executable instructions to:

synchronize a scanning of a target by the broadband imaging device with a generation of a plurality of light signals, from the plurality of broadband illumination sources, directed towards the target;

generate a set of spectral information associated with the target, based on the scanning of the target with the broadband imaging device;

generate a set of multispectral imaging (MSI) information associated with the target, based on performing an MSI operation using at least the set of spectral information, the MSI operation comprising:

generating a first set of spectral base functions, based on convolving one or more first parameters of the illumination device with one or more second parameters of the broadband imaging device;

generating a second set of spectral base functions, based on a spectral decomposition of the first set of spectral base functions; and determining a respective band approximation for each of the second set of spectral base functions; and determine ophthalmic information based on the set of MSI information.

2. The system of claim 1, wherein the processor is configured to execute the executable instructions to synchronize the scanning of the target with the generation of the plurality of light signals by synchronizing a modulation of an intensity of each of the plurality of broadband illumination sources with the scanning of the target.

3. The system of claim 2, wherein the scanning of the target is synchronized with the modulation of the intensity of each of the plurality of broadband illumination sources, such that each image frame captured by the broadband imaging device includes return light from only one of the plurality of light signals.

4. The system of claim 2, wherein the scanning of the target is synchronized with the modulation of the intensity of each of the plurality of broadband illumination sources, such that each scanning line of an image frame captured by the broadband imaging device includes return light from only one of the plurality of light signals.

5. The system of claim 1, wherein a number of spectral base functions in the second set of spectral base functions is less than a number of spectral base functions in the first set of spectral base functions.

6. The system of claim 1, wherein the processor is configured to execute the executable instructions to perform the MSI operation by further:

generating a reconstruction of the spectral information using the band approximations; and generating a comparison of the reconstruction of the spectral information with the spectral information.

7. The system of claim 6, wherein the processor is configured to execute the executable instructions to perform the MSI operation by further determining another respective band approximation for each of the second set of spectral base functions when the comparison satisfies a predetermined condition.

8. The system of claim 6, wherein the processor is configured to execute the executable instructions to transmit the MSI information for at least one of display or processing, when the comparison satisfies a predetermined condition.

9. The system of claim 1, wherein the ophthalmic information comprises one or more parameters of ocular tissue related to a physiological state of the ocular tissue.

10. The system of claim 1, wherein the ophthalmic information comprises a visualization of a subset of the MSI information.

11. A computer-implemented method comprising:

synchronizing a scan of a target by a broadband imaging device with a generation of a plurality of light signals, from a plurality of broadband illumination sources, directed towards the target;

generating a set of spectral information associated with the target, based on the scan of the target with the broadband imaging device;

generating a set of multispectral imaging (MSI) information associated with the target, based on performing an MSI operation using at least the set of spectral information, the MSI operation comprising:

generating a first set of spectral base functions, based on convolving one or more first parameters of the broadband illumination sources with one or more second parameters of the broadband imaging device;

generating a second set of spectral base functions, based on a spectral decomposition of the first set of spectral base functions; and determining a respective band approximation for each of the second set of spectral base functions; and determining ophthalmic information based on the set of MSI information.

12. The computer-implemented method of claim 11, wherein synchronizing the scan of the target with the generation of the plurality of light signals comprises synchronizing a modulation of an intensity of each of the plurality of broadband illumination sources with the scan of the target.

13. The computer-implemented method of claim 12, wherein the scan of the target is synchronized with the modulation of the intensity of each of the plurality of broadband illumination sources, such that each image frame captured by the broadband imaging device includes return light from only one of the plurality of light signals.

14. The computer-implemented method of claim 12, wherein the scan of the target is synchronized with the modulation of the intensity of each of the plurality of broadband illumination sources, such that each scanning line of an image frame captured by the broadband imaging device includes return light from only one of the plurality of light signals.

15. The computer-implemented method of claim 11, wherein a number of spectral base functions in the second set of spectral base functions is less than a number of spectral base functions in the first set of spectral base functions.

16. The computer-implemented method of claim 11, wherein performing the MSI further comprises:

generating a reconstruction of the spectral information using the band approximations; and generating a comparison of the reconstruction of the spectral information with the spectral information.

17. The computer-implemented method of claim 16, wherein performing the MSI operation further comprises determining another respective band approximation for each of the second set of spectral base functions when the comparison satisfies a predetermined condition.

18. A non-transitory computer-readable medium having computer executable instructions stored thereon, the computer executable instructions being executable by one or more processors to perform an operation comprising:

synchronizing a scan of a target by a broadband imaging device with a generation of a plurality of light signals, from a plurality of broadband illumination sources, directed towards the target;

generating a set of spectral information associated with the target, based on the scan of the target with the broadband imaging device;

generating a set of multispectral imaging (MSI) information associated with the target, based on performing an MSI operation using at least the set of spectral information, the MSI operation comprising:

generating a first set of spectral base functions, based on convolving one or more first parameters of the broadband illumination sources with one or more second parameters of the broadband imaging device;

generating a second set of spectral base functions, based on a spectral decomposition of the first set of spectral base functions; and determining a respective band approximation for each of the second set of spectral base functions; and determining ophthalmic information based on the set of MSI information.

* * * * *